United States Patent
Lancelle et al.

(10) Patent No.: US 11,083,552 B2
(45) Date of Patent: Aug. 10, 2021

(54) RENDERING OF DENTAL MODELS

(71) Applicant: Ivoclar Vivadent AG, Schaan (LI)

(72) Inventors: Marcel Lancelle, Zürich (CH); Roland Mörzinger, Zürich (CH); Nicolas Degen, Erlenbach (CH); Gabor Sörös, Zürich (CH); Bartolovic Nemanja, Zürich (CH)

(73) Assignee: Ivoclar Vivadent AG, Schaan (LI)

( * ) Notice: Subject to any disclaimer, the term of this patent is extended or adjusted under 35 U.S.C. 154(b) by 46 days.

(21) Appl. No.: 16/279,206

(22) Filed: Feb. 19, 2019

(65) Prior Publication Data

US 2019/0254791 A1 Aug. 22, 2019

(30) Foreign Application Priority Data

Feb. 20, 2018 (EP) .................................... 18157574
Feb. 21, 2018 (EP) .................................... 18157809
Sep. 28, 2018 (EP) .................................... 18197524

(51) Int. Cl.
*A61C 13/34* (2006.01)
*A61C 9/00* (2006.01)
(Continued)

(52) U.S. Cl.
CPC .............. *A61C 13/34* (2013.01); *A61B 90/36* (2016.02); *A61C 5/77* (2017.02); *A61C 9/0053* (2013.01); *A61C 13/0019* (2013.01); *A61B 5/4547* (2013.01); *A61B 2034/102* (2016.02); *A61B 2034/105* (2016.02); *A61B 2090/365* (2016.02); *A61C 7/002* (2013.01); *A61C 13/0004* (2013.01);
(Continued)

(58) Field of Classification Search
CPC ......... G06T 2207/30036; G06T 19/006; A61C 9/0053; A61C 7/002; A61C 13/0004; A61B 2090/365; A61B 5/4547; G16H 50/50
USPC .......................................... 345/426, 629–641
See application file for complete search history.

(56) References Cited

U.S. PATENT DOCUMENTS 5,515,109 A * 5/1996 Vlahos ................... H04N 5/272
348/586
7,717,708 B2 5/2010 Sachdeva et al.
(Continued)

OTHER PUBLICATIONS

Amirkhanov, Aleksandr et al., "WithTeeth: Denture Preview in Augmented Reality," Eurographics Proceedings, The Eurographics Association, pp. 1-10, 2018.
(Continued)

*Primary Examiner* — Mark K Zimmerman
*Assistant Examiner* — Jonathan M Cofino
(74) *Attorney, Agent, or Firm* — Ann Knab; Thad McMurray (57) ABSTRACT

The invention pertains to a method for realistic visualization of a 3D virtual dental model (1) in a 2D image (20) of a face, the method comprising estimating or assuming a lighting situation in the image of the face, determining boundaries of an inner mouth region in the image, computing, based on the boundaries of the inner mouth region, on a 3D face geometry and on the lighting situation, a shadowing in the inner mouth region, computing a lighting of the dental model (1) based at least on the computed shadowing, and visualizing the dental model (1) and the 2D image (20), wherein at least the inner mouth region in the image is overlaid with a visualization (21) of the dental model having the computed lighting.

14 Claims, 3 Drawing Sheets

(51) Int. Cl.
*A61C 13/00* (2006.01)
*A61B 90/00* (2016.01)
*A61C 7/00* (2006.01)
*G16H 50/50* (2018.01)
*A61B 5/00* (2006.01)
*A61C 5/77* (2017.01)
*B33Y 80/00* (2015.01)
*A61B 34/10* (2016.01)

(52) U.S. Cl.
CPC ..... *B33Y 80/00* (2014.12); *G06T 2207/30036* (2013.01); *G16H 50/50* (2018.01)

(56) References Cited

U.S. PATENT DOCUMENTS

| | | | |
|---|---|---|---|
| 9,775,491 B2 | 10/2017 | Clausen et al. | |
| 2004/0029068 A1* | 2/2004 | Sachdeva | A61C 9/0046 433/24 |
| 2007/0273765 A1* | 11/2007 | Wang | G06K 9/38 348/152 |
| 2011/0125304 A1* | 5/2011 | Schneider | A61C 13/0004 700/98 |
| 2011/0212420 A1 | 9/2011 | Vuillemot | |
| 2012/0287130 A1* | 11/2012 | Rhee | G06T 15/50 345/426 |
| 2013/0060532 A1 | 3/2013 | Clausen et al. | |
| 2013/0158958 A1 | 6/2013 | Methot | |
| 2013/0218530 A1* | 8/2013 | Deichmann | G06F 30/00 703/1 |
| 2015/0350517 A1* | 12/2015 | Duret | H04N 5/2256 348/66 |
| 2016/0015246 A1* | 1/2016 | Clausen | A61B 1/00009 433/29 |
| 2017/0109931 A1* | 4/2017 | Knorr | G06T 7/11 |
| 2017/0319293 A1 | 11/2017 | Fisker | |
| 2018/0025529 A1* | 1/2018 | Wu | A61B 5/1077 345/426 |
| 2019/0125492 A1* | 5/2019 | Lin | A61C 7/002 |

OTHER PUBLICATIONS

Hughes, John F. et al., "Computer Graphics, Principles and Practice," Book, Third Edition, pp. 101-103, 112-115, 120-130, and 412-417, Jul. 2013, Addison-Wesley.

Akenine-Möller, Tomas, et al., "Real-Time Rendering," Book, Third Edition, pp. 110-116, Ch. 7, pp. 201, Ch. 9 pp. 327-373, 2008, A K Peters, Ltd./CRC Press.

Wikipedia, https://en.wikipedia.org/wiki/Shading, "Shading", pp. 1-6, Retrieved on Mar. 18, 2021.

* cited by examiner

RENDERING OF DENTAL MODELS

CROSS-REFERENCE TO RELATED APPLICATIONS

This application claims priority to European patent application No. 18197524.4 filed on Sep. 28, 2018, European patent application No. 18157574.7 filed on Feb. 20, 2018, and European patent application No. 18157809.7 filed on Feb. 21, 2018, all the disclosures of which are incorporated herein by reference in their entirety.

TECHNICAL FIELD

The present invention pertains to a computer-implemented method for realistic visualization of three-dimensional models of a denture or other dental prosthesis (dental model) in an image or image stream of a person's face. In particular, the described method allows realistic visualization of dental models in dental virtual mock-up applications, such as dental augmented reality applications.

In the context of the present invention, the term "denture" is not necessarily restricted to full dentures but also comprises partial dentures, orthodontic situations or adaptations, or dental restorations such as dental prostheses, including crowns, crown lays, veneers, inlays and onlays, bridges, dental implants, and implant restorations. Accordingly, the term "dental model" includes all models of dental prostheses—such as models of complete and partial dentures—that are used for prosthodontic purposes. The dental model may also comprise appliances that are attached to dentures or real teeth, such as dental braces and retainers or mouthguards for several purposes.

For dentists and patients, it is of interest to get a visual impression of the appearance of the patient's face with a modified dental situation, i.e. to visualize the modified dental situation in an image of the face of the patient. Also, the appearance during or after a dental treatment may be of importance for the patient before deciding to undergo such treatment. For this purpose, a virtual preview (virtual mock-up) of the dentition modified by dental treatment is helpful for the dentist and may also be used in the course of interactively modifying the treatment plan to get the most favourable aesthetic results.

BACKGROUND

In dental virtual mock-up applications, virtual teeth are shown in a photo or video of a person's face or part thereof. Realistic visualization is important in this field, as humans are very sensitive to deviations from reality in human faces. This is a well-known problem called the "uncanny valley".

To overcome the "uncanny valley" problem in a visualization of virtual teeth in a photo or video of a face, realistic lighting of the three-dimensional (3D) rendered content is crucial. Thus, the lighting of the rendered virtual content should match the lighting of the real scene—i.e. essentially the face. So far, no such lighting exists for the application in rendering 3D virtual dentition in dentistry.

In computer game rendering of virtual characters, the character's 3D face geometry is used for generating lighting and shadowing effects. Images or videos of a face however are two-dimensional (2D) and thus do not provide a 3D face geometry.

Another typical solution for this problem includes ray tracing. This enables realistic rendering by taking many physical effects into account. However, this approach is usually too slow for real time applications.

U.S. Pat. No. 9,775,491 B2, which is hereby incorporated by reference in its entirety, discloses a computer implemented method for visualizing an image rendered from a three-dimensional model of a dental situation to an image of the face of the patient recorded by a camera. In this method a three-dimensional model of the oral cavity of the patient is obtained. This three-dimensional model is modified in a dentistry treatment plan by applying dental restorations to obtain a three-dimensional model of the dental situation of the patient dentition after application of the dental restorations. A two-dimensional image of the face of the patient including the mouth opening is obtained. Then the positioning of the camera that recorded the image relative to the dentition of the patient is estimated. In this application "positioning of the camera" meant to include the three-dimensional position x, y, z in space and the angular orientation of the camera with respect to the face of the patient. A virtual camera using the estimated positioning is processing the three-dimensional model of the dental situation to obtain a two-dimensional image, and a portion of the three-dimensional model of the dental situation is selected which is visible to the virtual camera. The image rendered by the virtual camera is overlaid and displayed in the image taken by the camera.

Similar methods are set forth in US 2011212420 directed to a method of forming a dental mold, US 20130060532 directed to a method of composing and designing teeth, US 2013158958 directed to a dental analysis method and system, US 20170319293 directed to a method of digitally designing a modified dental setup, and U.S. Pat. No. 7,717,708 directed to computer-based methods for supporting dentists during dental treatment planning for a patient, all of which are hereby incorporated by reference in their entirety.

SUMMARY

It is therefore an object of the present invention to provide a computer-implemented method that allows realistic rendering and illumination of a virtual three-dimensional dental model, particularly being a representation of a full or partial denture.

It is another object to provide such a method, wherein the resulting rendering of the virtual dental model fits into to a camera image of a face.

It is another object to provide such a method that allows overcoming the uncanny valley problem.

It is another object to provide such a method that allows realistic rendering and illumination of the model in real-time.

It is another object to provide such a method that allows realistic rendering and illumination of the model in augmented-reality (AR) applications.

It is another object to provide such a method that can be performed on a mobile device with limited computing power, particularly in real time and/or with a live video feed.

It is another object to provide such a method that is performed fully or semi-automatically.

It is a further object to provide a handheld mobile device for performing such a method.

At least one of these objects is achieved by the method of claim 1, the mobile device of claim 14 and/or one of the dependent claims of the present application.

A first aspect of the invention relates to a method for realistic visualization of a virtual dental model in a two-dimensional image of a face, the image comprising at least an inner mouth region of the face. The dental model comprises a three-dimensional representation of a dental prosthesis (or part thereof). For instance, the model can be that of a full or partial denture. In particular, the dental model is a digital three-dimensional model of a denture comprising one or more teeth, in particular a plurality of teeth, e. g. six or more teeth, with or without gum (gingiva).

The method comprises estimating or assuming a lighting situation in the image of the face and determining boundaries of the inner mouth region in the image, particularly wherein the boundaries are defined by inner boundaries of lips of the face. The lighting situation comprises one or more light sources, in particular also a position of the light sources, image based or global illumination, spherical harmonics or directional lights.

Based on the boundaries of the inner mouth region, on a three-dimensional face geometry and on the lighting situation, a shadowing in the inner mouth region (or spatially: in the region behind the inner mouth region) is computed. Based at least on the computed shadowing, a lighting of the dental model is computed. Finally, the 3D dental model and the 2D image are visualized together, the visualization of the dental model (e. g. a 2D representation of the dental model) having the computed lighting. In particular, at least the inner mouth region in the image is overlaid with the visualization of the dental model.

According to one embodiment of the method, the three-dimensional face geometry is a geometry of the face, i.e. the same face that is shown in the image, wherein the face geometry is acquired using a depth sensor. In particular, the three-dimensional face geometry can be acquired together with the two-dimensional image or as a range image.

According to an alternative embodiment of the method, the three-dimensional face geometry at least approximates a geometry of a human face (or at least of the mouth region), wherein an image plane comprising at least the boundaries of the inner mouth region is projected onto the three-dimensional geometry. In particular, the three-dimensional face geometry may comprise at least a part of a side surface of a cylinder or prism, onto which part of the side surface an image plane of at least the part of the image comprising the mouth region is projected.

According to one embodiment of the method, computing the lighting comprises
  generating, for a multitude of surface points (e. g. vertices of the virtual dental model) on the surface of the virtual dental model, a first ray to each of a plurality of virtual point light sources,
  generating for each first ray a second ray to a virtual camera, using an intersection of the first ray with the three-dimensional geometry as a starting point for the second ray, and
  using an intersection of the second ray with an image plane as a lookup location to determine a lighting for the respective surface point, wherein a surface point is assumed to be lighted by a virtual point light source if the second ray intersects the image plane at the inner mouth region.

According to another embodiment of the method, visualizing the dental model in the two-dimensional image also comprises adapting a colouring of the dental model based on a colouring of the image.

In one embodiment adapting the colouring comprises identifying, for at least one of teeth, gum and lips, a reference colour in the image. For instance, said reference colour can be an average colour, and identifying a reference colour may comprise performing an automatic segmentation of image pixels relating to teeth, gum and/or lips in the image. The reference colour or reference colours are used for estimating a colour space of the image. The estimated colour space of the image is used to transform a colour space of the dental model. In particular, the estimated colour space of the image is used as colour space of the dental model.

For instance, the colour space of the dental model can be transformed to match the colour space of the image.

According to another embodiment of the method, the lighting of the dental model is computed based on an estimated lighting situation. The lighting situation can be estimated based on the lighting of the face in the image.

In one embodiment estimating the lighting situation comprises
  estimating low frequency lighting, particularly with spherical harmonics or virtual point lights, and/or
  detecting reflections in eyes of the face to estimate a position of light sources, particularly high frequency lighting.

According to another embodiment of the method, a soft or blurred edge of the inner mouth region is calculated from the determined boundary, wherein computing the shadowing is based on the soft or blurred edge in order to avoid hard shadow edges.

According to another embodiment of the method, computing the lighting of the dental model comprises applying lighting and shading effects, the effects comprising at least one of specular reflections, colours and ambient occlusion.

According to another embodiment of the method, visualizing the dental model comprises simulating camera effects to approximate an appearance of the dental model to the appearance of the face in the image, the simulated camera effects comprising at least one of dynamic range, contrast, saturation, noise, lens distortion, white balance, defocus blur and motion blur.

According to another embodiment of the method, the image is part of an image stream, and the method is performed in real time for at least a multitude of images of the image stream.

According to one embodiment, visualizing the dental model in the two-dimensional image comprises adapting a colouring of the dental model based on a colouring of a plurality of images of the image stream, for instance comprising the actual image and previous images of the image stream, in particular wherein mean values from a plurality of consecutive images are used for adapting the colouring.

According to another embodiment, the method further comprises capturing the image stream by means of a camera and visualizing the dental model and the two-dimensional image on a displaying device to a user, particularly wherein the face is the face of the user.

According to a further embodiment, the camera and the displaying device are part of the same mobile device, wherein the method is performed by means of one or more algorithms installed on a computing unit of the mobile device.

According to another embodiment of the method, the virtual dental model is in a polygon mesh format and comprises a plurality of vertices. Computing the lighting of the dental model optionally comprises computing a shading. This computing of the shading may be performed in a vertex shader and/or locally per vertex or per fragment.

A second aspect of the invention pertains to a mobile device comprising a camera and a display that arranged so that images of a user's face are capturable by the camera while the user watches the display—i.e. for instance a Smartphone having a "selfie camera". The device comprises a computing unit with at least one algorithm that is adapted to perform the method according to the first aspect. In particular, the image with the overlaid visualization of the model is displayable on the display.

A further aspect of the invention pertains to a computer programme product comprising programme code which is stored on a machine-readable medium, or being embodied by an electromagnetic wave comprising a programme code segment, and having computer-executable instructions for performing the method according to the first aspect.

BRIEF DESCRIPTION OF THE DRAWINGS

The invention in the following will be described in detail by referring to exemplary embodiments that are accompanied by figures, in which.

DETAILED DESCRIPTION

Figure 1:
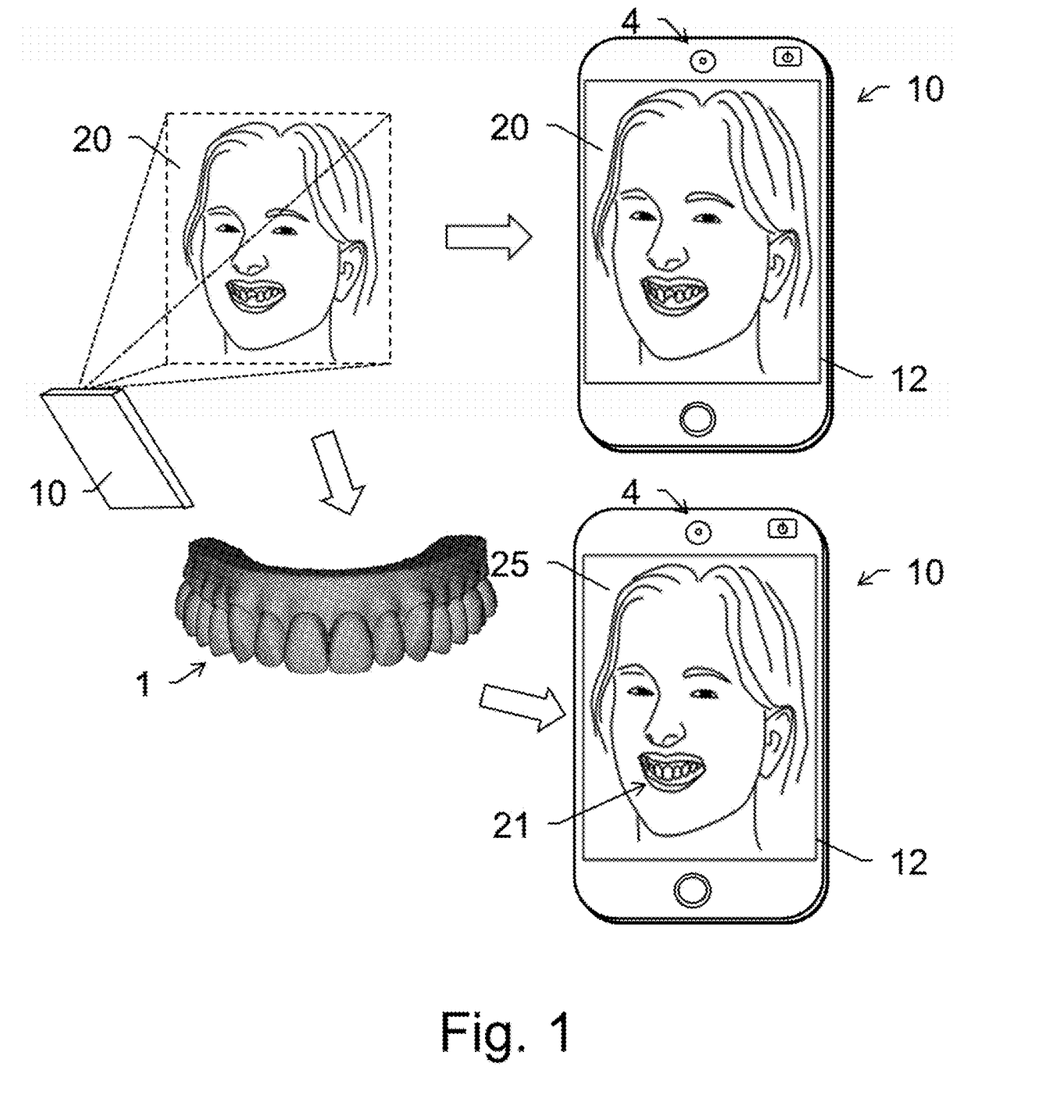
FIG. 1 illustrates an exemplary embodiment of a computer-implemented method for realistic visualization of a 3D dental model in an image of a person's face.

FIG. 1 illustrates a computer-implemented method for realistic visualization of a 3D dental model in an image of a person's face according to an exemplary embodiment of the invention.

According to the shown embodiment, an image 20 of the person's face is captured by means of a camera 4. In this embodiment, the camera 4 is part of a handheld mobile device 10 such as a smartphone. The device 10 comprises a display 12 which is enabled to display the image 20 in real time to the user, i.e. the person whose image is captured. Data of a three-dimensional (3D) virtual dental model 1 is provided in a data storage of the mobile device 10. An algorithm being provided in a computing unit of the mobile device 10 is adapted to fit the dental model 1 into the image to provide an augmented-reality (AR) image 25 on the display 12, wherein the rendered dental model 21 (e. g. a 2D visualization of the model) is displayed in the inner mouth region of the face. The processing can be performed offline on an image or video or in real time on a live camera image thus providing a live augmented-reality application.

In some embodiments, the dental model 1 may comprise appliances that are attached—either temporarily or permanently—to dentures or real teeth of the dental model 1, such as dental braces and retainers or mouthguards for several purposes. In some embodiments the dental model 1 comprises only these appliances or only the appliances of the model are visualized in the image.

In the field of artificial dentition, the rendering of digital dental models 1 without realistic lighting information leads to unsatisfactory results. Realistic visualization is important in this field, as humans are very sensitive to even slight deviations from reality in human faces. To overcome this "uncanny valley" problem in a visualization of virtual teeth in a photo or video of a face, realistic lighting of the 3D rendered content is crucial. According to the disclosed invention, the realism may be achieved by rendering of shadows and optionally by also applying colour correction, so that the lighting of the rendered virtual content should match the lighting of the real scene—i.e. essentially the face.

For calculating a shadowing, in one embodiment, a given or constant lighting situation simply may be assumed. For more realistic results, alternatively, an approximate lighting situation in the image can be detected. The lighting can be estimated using the face as a light probe to obtain an approximation of the lighting of the face. Both, low frequency lighting—e. g. with spherical harmonics or virtual point lights—and high frequency lighting for reflections (e. g. from the eyes) can be estimated.

Figure 2:
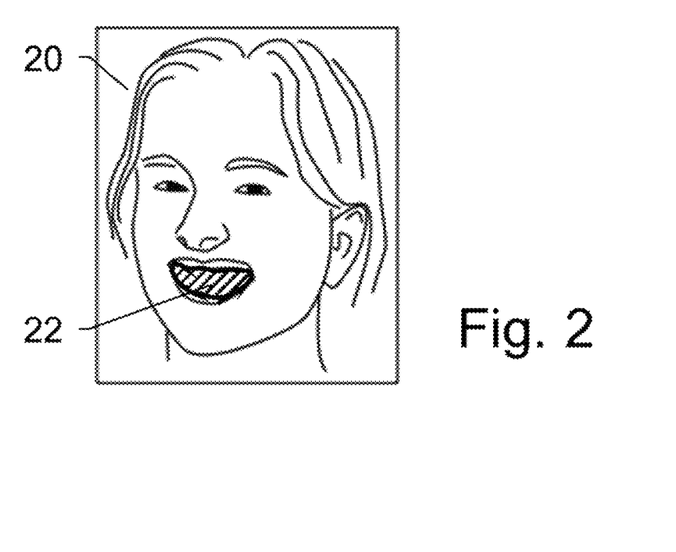
FIG. 2 shows an inner mouth area identified in the image.

According to the present invention, shadowing can be calculated even without having a detailed 3D model of the face. According to some embodiments of the invention, the 2D image of an inner mouth region 22 (e. g. a binary 2D mouth mask image) is used as a 3D occluder. In these embodiments, as illustrated in FIG. 2, adding realistic lighting to the dental model 1 comprises identifying the boundaries of the inner mouth region 22 in the imaged face. In the exemplary embodiment of FIG. 2, the inner mouth region 22 comprises that part of the imaged face that lies inside the lips. The inner mouth region 22 can either be defined by the user, e. g. by selecting the area in the image 20, or be automatically identified by means of a feature recognition algorithm.

Having identified the boundaries of the inner mouth region 22, these can be used to calculate light and shadow in the area behind the inner mouth region 22, i.e. the area where the dentition corresponding to the virtual model 1 would be placed in reality. The method makes use of a 3D mouth contour to cast shadows. Optionally, this is followed by applying a colour correction to match the camera image properties such as white balance, brightness, saturation, contrast etc. This is illustrated in the following FIGS. 3, 4 and 5.

If the 2D image is captured together with depth information, e. g. using a depth sensor, the available 3D information of the face can be used to provide the needed 3D mouth contour.

If only a two-dimensional (2D) mouth region is available from the 2D image, the mouth region and the surrounding part of the face need to be brought to 3D. To do so, according to the embodiment of the method illustrated in FIG. 3, at least the inner mouth region or a shape thereof is projected onto a 3D geometry 2 that approximates a geometry of a human face. In particular, the geometry 2 may be the side face of a cylinder or prism.

Figure 3:
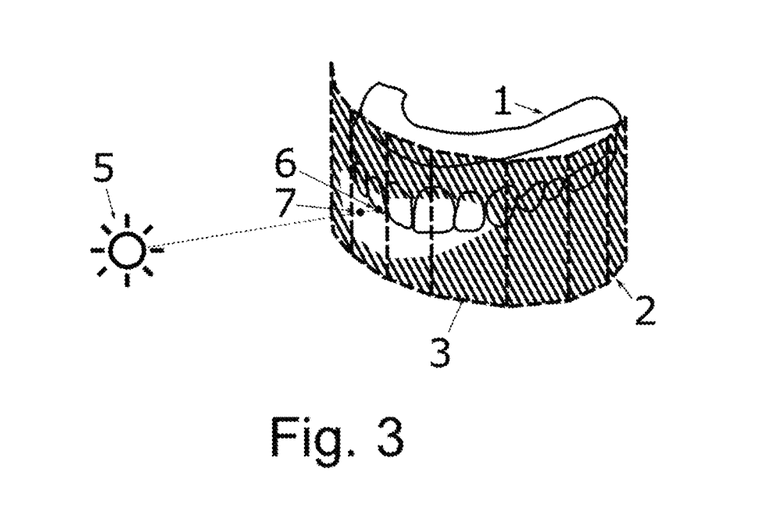
FIG. 3 illustrates determining realistic lighting of the dental model according to a first exemplary embodiment of the method.

Alternatively, a 3D facial model with explicit face geometry can be generated to cast shadows. The known 2D boundaries of the inner mouth region 22 that has been projected to 3D can then be used for calculating 3D lighting and shadowing.

Having assumed or estimated a position of a light source 5 relative to the face in the image, its position relative to each point of the projection 3 of the inner mouth region can be determined. The model 1 is positioned behind the mouth region in a position the real dentition would be placed in a real mouth. Assuming that the 3D pose of the virtual dental model 1 is known, e. g. based on deep learning approaches or facial landmarks with a 3D head pose estimation, the camera parameters to render the 3D model 1 are given. Accordingly, the model 1 can be positioned behind the projection with the correct pose.

For a multitude of points 6 of the model 1, it is then determined whether an interjection 7 of a ray originating in the light source 5 with the 3D geometry 2 lies within the inner mouth region. If it does, the point 6 is lighted by the light source 5, if not, the point is shadowed by the face. If the virtual dental model 1 is in a polygon mesh format the points can be vertices or fragments. The lighting of the virtual dental model 1 can be computed locally to take both the estimated lighting as well as the shadowing from the exterior of the mouth region into account.

The boundaries of the defined mouth region optionally can be embedded as soft or blurred edges to avoid unrealistic hard shadow edges, especially if point-shaped virtual lights sources are used. In addition, other lighting and shading can be applied, such as specular reflections, colours or ambient occlusion. Optionally, further camera effects can be simulated to provide a more realistic appearance of the rendered model. The camera effects comprise, for instance, dynamic range, contrast, saturation, noise, lens distortion, white balance, defocus or motion blur.

Figure 4:
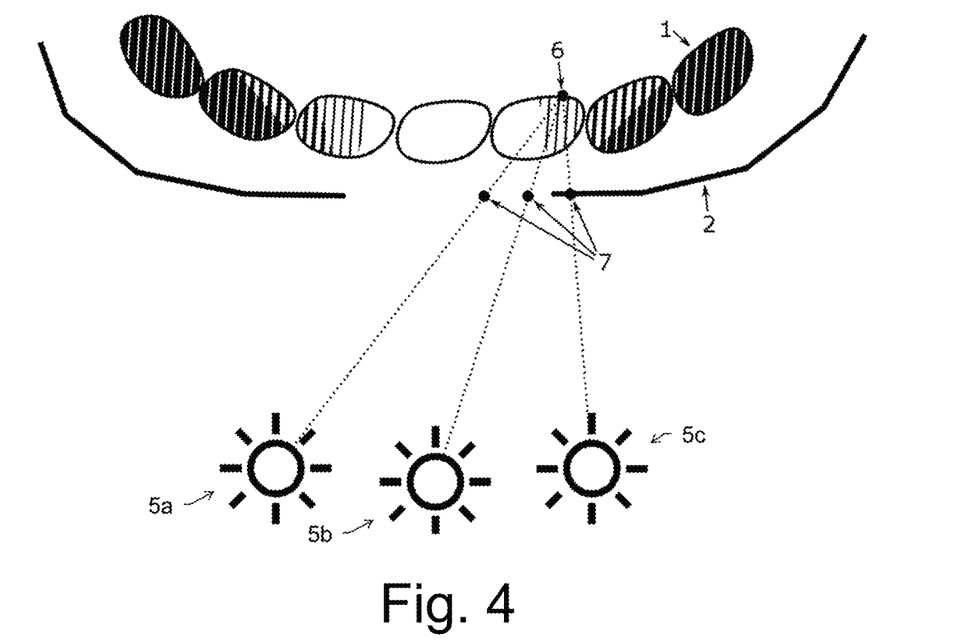
FIG. 4 illustrates determining realistic lighting of the dental model according to a second exemplary embodiment of the method.

FIG. 4 illustrates another embodiment of the method, showing the dental model 1 and 3D geometry 2 in a cross sectional view. For a point 6 on the surface of the model 1, intersections 7 of three rays originating from three light sources 5*a*-*c* are tested on their position inside or outside the inner mouth region. Here, the intersections 7 of rays from light sources 5*a* and 5*b* are inside the inner mouth region, and the intersection 7 related to light source 5*c* is not. This means that point 6 is lighted only by two of the three light sources (i.e. light sources 5*a* and 5*b*).

The model 1 has four different brightness levels. These depend on how many of the three light sources 5*a*-*c* illuminate a point or portion of the model 1. The highest brightness is in the centre of the model, where all three light sources 5*a*-*c* illuminate the surface of the dental model 1. Point 6 lies in an area having the second brightness level. The third brightness level is illuminated only by one of the light sources 5*a*-*c*, and the fourth brightness level is completely shadowed by the face when projected on the 3D geometry.

It is important to provide the correct brightness to each of the several brightness levels, i.e. not to visualize the rendered model or parts thereof too dark or too bright to look realistic. Therefore, the method may optionally comprise a step of detecting a lighting situation of the mouth background in the image, e. g. by how far the inside of the mouth cavity is darker than the outside of the face. To do so, the darkest point of the mouth background may be determined to serve as a reference for the shadowing. Additionally or alternatively, a contrast level of the camera image may be detected.

Figure 5:
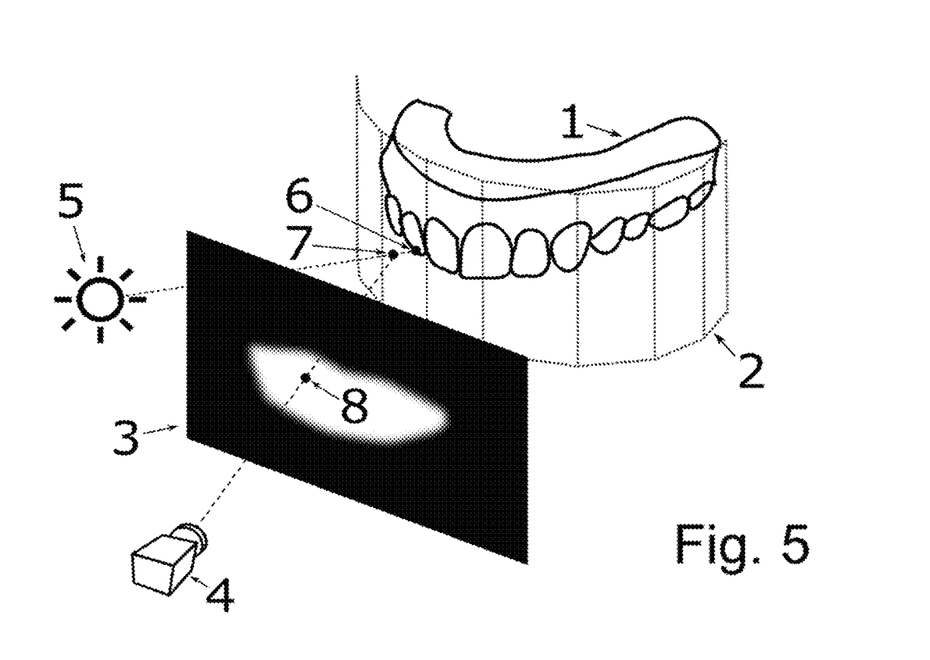
FIG. 5 illustrates determining realistic lighting of the dental model according to a third exemplary embodiment of the method.

FIG. 5 illustrates another embodiment of determining realistic lighting for the dental model 1. This embodiment comprises performing the lighting computation in the vertex shader. For each vertex 6 a ray to each virtual point light source 5 is generated. Its intersection 7 with the face proxy geometry 2 (e. g. a cylinder) is used to create a ray to the (virtual) camera 4. Its projection 8 into the image plane 3 is the lookup location to determine whether the light is visible through the inner mouth region, i.e. not occluded by lips or facial tissue.

Having added lighting information to the model, the rendered 3D model is overlaid on the photo only within the defined mouth region. Also, colours can be adapted such that the 3D rendered content matches the camera image. One way to match colours is to automatically find an average teeth colour and/or an average gum or lip colour in the image. They can be obtained from an automatic segmentation of tooth pixels and gum and lip pixels. These average colours serve as reference colours and can be used to transform the colour space to the one estimated from the camera image. Of course, instead of using average colours, reference colours can also be derived using minimum and/or maximum values or histograms.

If a video is rendered instead of a single image, to avoid flickering over time, reference colours from previous frames can be taken into account, e. g. by temporally smoothing the values.

In an exemplary embodiment, a method is provided for realistic visualization of a virtual dental model in an image of a face. The method comprises obtaining a virtual dental model. The virtual dental model includes a three-dimensional representation of a dental object to be visualized, for example, a denture or other dental prosthesis, braces, mouth guard, jewelry, etc. An assumed, measured, or approximated lighting situation of the image is determined. For example, the method may include determining a position of at least one light source of the image used to illuminate the face of the image. An inner mouth region in the image is determined wherein the inner mouth region is defined by inner boundaries of lips of the face. In some embodiments, the inner mouth region is determined using a processor. A processor is used to compute a shadow in the inner mouth region based on a face geometry and the determined lighting situation (e.g., the position of the at least one light source). The face geometry may be, for example, an approximated face geometry. A lighting of the dental model is computed using the processor, wherein the lighting is based on the computed shadow in the inner mouth region. The dental model is displayed on a display with the computed lighting applied and wherein the dental model is shown within the inner mouth region of the image.

In the context of the present invention, the term "denture" is not necessarily restricted to full dentures but also comprises partial dentures or orthodontic situation/adaptations or dental restorations such as dental prostheses, including crowns, crown lays, veneers, inlays and onlays, bridges, dental implants, implant restorations. Accordingly, the term "dental model" includes all models of dental prostheses as well as the patient situation that could be partial or fully edentulous—such as models of complete and partial dentures—that are used for prosthodontic purposes.

In some embodiments, the present disclosure is implemented using a system having a camera, a processor, an electronic data storage unit, and a display. The camera can be a standard camera, an infrared dot-projection detector, flood illuminator camera, structured-light three-dimensional scanner, standard infrared detector, ultrasonic imaging device, Doppler detector, or any other suitable visualization system capable of capturing information related to a patient's dentition. The processor can be a single processor having one or more cores, or a plurality of processors connected by a bus, network, or other data link. The electronic data storage unit can be any form of non-transitory computer-readable storage medium suitable for storing the data produced by the system. The display can be any display suitable for displaying a digital color or grayscale image.

In some embodiments, the camera, processor, electronic data storage unit, and digital display are components of a single device. The single device may be a smartphone, tablet, laptop computer, personal digital assistant, or other computing device.

In some embodiments, the processor is in communication over a network, which could be wired or wireless, with an external processor used for performing one or more calculation steps and/or a network-attached electronic data storage unit. In some embodiments, the present disclosure makes use of cloud computing to perform one or more calculations steps remotely and/or remote storage to enable the storage of data remotely for collaborative or remote analysis. In some embodiments, the system comprises a plurality of graphical user interfaces to permit multiple users to view or analyze the same data.

In some embodiments, the system operates to provide one or more users with a visualization of a virtual dental model of a patient's teeth, which may be altered to visualize the effect of one or more dental or orthodontic alterations. In some embodiments, this allows the one or more users to visualize a "before" dentition image, i.e., the appearance of a patient's dentition prior to a dental or orthodontic procedure, and an "after" dentition image, i.e., a representation of the expected appearance of a patient's dentition after a proposed dental or orthodontic procedure.

In some embodiments, the system operates by capturing information related to a patient's dentition using a camera, creating a model of the patient's dentition on a processor, fitting a model of a proposed post-alteration dentition to the patient's dentition on the processor, coloring the model of the proposed post-alteration dentition to match an expected real post-alteration coloration, and displaying the fitted model of the proposed post-alteration dentition in place of the patient's actual dentition on a display which otherwise shows the patient's actual facial features. The information related to a patient's dentition, the model of the patient's dentition, and the model of the proposed post-alteration dentition may be stored on an electronic data storage unit. In some embodiments, the operations are performed in real-time.

In some embodiments, a user interface is configured such that a user may view the "before" dentition image and the "after" dentition image simultaneously either side-by-side or with a full or partial overlay.

Where used herein, the term "non-transitory" is a limitation on the computer-readable storage medium itself—that is, it is tangible and not a signal—as opposed to a limitation on the persistence of data storage. A non-transitory computer-readable storage medium does not necessarily store information permanently. Random access memory (which may be volatile, non-volatile, dynamic, static, etc.), read-only memory, flash memory, memory caches, or any other tangible, computer-readable storage medium, whether synchronous or asynchronous, embodies it.

Although the invention is illustrated above, partly with reference to some preferred embodiments, it must be understood that numerous modifications and combinations of different features of the embodiments can be made. All of these modifications lie within the scope of the appended claims.

The invention claimed is:

1. A method for realistic visualization of a virtual dental model (1) in a two-dimensional image (20) of a face, the image comprising at least an inner mouth region (22) of the face, the dental model (1) comprising a three-dimensional representation of a denture or other dental prosthesis, the method comprising:
    estimating or assuming a lighting situation in the image (20) of the face, the lighting situation comprising one or more light sources (5),
    determining boundaries of the inner mouth region (22) in the image, particularly wherein the boundaries are defined by inner boundaries of lips of the face,
    projecting the boundaries of the inner mouth region to a three-dimensional face geometry (2) that approximates the geometry of a human face,
    computing, based on the projected boundaries of the inner mouth region (22) on the three-dimensional face geometry (2) and on the lighting situation, a shadowing in the inner mouth region (22),
    computing a lighting of the dental model (1) based at least on the computed shadowing, and
    visualizing the dental model (1) and the two-dimensional image (20), wherein a visualization (21) of the dental model (1) has the computed lighting.

2. The method according to claim 1, characterized in that
    the three-dimensional face geometry (2) comprises at least a part of a side surface of a cylinder or prism, onto which part of the side surface an image plane (3) of at least the part of the image comprising the mouth region is projected.

3. The method according to claim 1, characterized in that
computing the lighting comprises
    generating, for a multitude of surface points (6) on the surface of the virtual dental model (1), a first ray to each of a plurality of virtual point light sources (5),
    generating for each first ray a second ray to a virtual camera, using an intersection (7) of the first ray with the three-dimensional face geometry (2) as a starting point for the second ray, and
    using an intersection (8) of the second ray with an image plane (3) as a lookup location to determine a lighting for the respective surface point (6), wherein a surface point (6) is assumed to be lighted by a virtual point light source (5) if the second ray intersects the image plane (3) at the inner mouth region (22),
particularly wherein the multitude of surface points (6) are vertices of the virtual dental model (1).

4. The method according to claim 1, characterized in that
visualizing the dental model (1) in the two-dimensional image (20) comprises adapting a colouring of the dental model (1) based on a colouring of the image (20), particularly wherein adapting the colouring comprises
    identifying, for at least one of teeth, gum and lips, a reference colour in the image (20), particularly wherein
    the reference colour is an average colour, and/or
    identifying a reference colour comprises performing an automatic segmentation of image pixels relating to teeth, gum and/or lips in the image (20),
    using the reference colour or reference colours for estimating a colour space of the image (20), and
    using the colour space of the image (20) to transform a colour space of the dental model (1), particularly wherein the colour space of the image (20) is used for the colour space of the dental model (1).

5. The method according to claim 1, characterized in that
the lighting of the dental model (1) is computed based on an estimated lighting situation, wherein the lighting situation is estimated based on the lighting of the face in the image (20), particularly wherein estimating the lighting situation comprises
    estimating low frequency lighting, particularly with spherical harmonics or virtual point lights, and/or detecting reflections in eyes of the face to estimate a position of light sources, particularly high frequency lighting.

6. The method according to claim 1, characterized in that a soft or blurred edge of the inner mouth region (22) is calculated from the determined boundary, wherein computing the shadowing is based on the soft or blurred edge in order to avoid hard shadow edges.

7. The method according to claim 1, characterized in that
computing the lighting of the dental model (1) comprises applying lighting and shading effects, the effects comprising at least one of specular reflections, colours and ambient occlusion; and/or
visualizing the dental model comprises simulating camera effects to approximate an appearance of the dental model (1) to the appearance of the face in the image (20), the simulated camera effects comprising at least one of dynamic range, contrast, saturation, noise, lens distortion, white balance, defocus blur and motion blur.

8. The method according to claim 1, characterized in that the image (20) is part of an image stream, and the method is performed in real time for at least a multitude of images (20) of the image stream.

9. The method according to claim 8, characterized in that visualizing the dental model (1) in the two-dimensional image (20) comprises adapting a colouring of the dental model (1) based on a colouring of a plurality of images (20) of the image stream, particularly comprising the actual image and previous images of the image stream, in particular wherein mean values from a plurality of consecutive images are used for adapting the colouring.

10. The method according to claim 8, characterized in that the method further comprises capturing the image stream by means of a camera (4) and visualizing the dental model (1) and the two-dimensional image (20) on a displaying device (12) to a user, particularly wherein the face is the face of the user.

11. The method according to claim 8, characterized in that the camera (4) and the displaying device (12) are part of the same mobile device (10), wherein the method is performed by means of one or more algorithms installed on a computing unit of the mobile device (10).

12. The method according to claim 1, characterized in that the virtual dental model (1) is in a polygon mesh format and comprises a plurality of vertices, particularly wherein computing the lighting of the dental model comprises computing a shading, wherein computing the shading is performed in a vertex shader and/or locally per vertex or per fragment.

13. A mobile device (10) comprising a camera (4) and a display (12) that arranged so that images (20) of a user's face are capturable by the camera (4) while the user watches the display (12), characterized in that the device comprises a computing unit with at least one algorithm that is adapted to perform the method of claim 1.

14. A computer programme product comprising programme code which is stored on a non-transitory machine-readable medium, the non-transitory machine-readable medium comprising computer instructions executable by a processor, which computer instructions cause the processor to perform the method according to claim 1.

* * * * *